United States Patent [19]
Barrelle et al.

[11] Patent Number: 5,944,699
[45] Date of Patent: Aug. 31, 1999

[54] PRE-ASSEMBLED SYRINGE

[76] Inventors: Laurent Barrelle, 31 Rue Nicolas Chorier, 38000 Grenoble; Philippe Jacon, 22 rue Ponsard, 38100, Grenoble, both of France

[21] Appl. No.: 08/909,428

[22] Filed: Aug. 11, 1997

[51] Int. Cl.⁶ ..................................................... A61M 5/00
[52] U.S. Cl. ........................................... 604/240; 604/263
[58] Field of Search ........................... 604/192, 239–243, 604/263

[56] References Cited

U.S. PATENT DOCUMENTS

| | | | |
|---|---|---|---|
| 4,747,835 | 5/1988 | Sandhaus | 604/192 |
| 4,961,730 | 10/1990 | Poncy | 604/198 |
| 5,451,213 | 9/1995 | Teicher et al. | 604/192 |
| 5,562,625 | 10/1996 | Stefancin, Jr. | 604/110 |

*Primary Examiner*—Corrine McDermott

[57] ABSTRACT

A prefilled syringe provides for secure assembly of the components prior to use. The syringe includes a hollow barrel having opposed open ends and a plunger manually operable within one of the ends of the barrel. An injection holder is attached to the other end of the barrel. An injection member such as a hypodermic needle assembly or an IV access device is removably secured to the injection holder. The cover accommodates the injection member and is removably attached to the injection holder. The cover is movable with respect to the injection holder from a first position where the cover is retained on the injection holder to a second position where the cover is removed from the injection holder. Movement of the cover from the first position to the second position assures the removable securement of the injection member to the injection holder.

28 Claims, 17 Drawing Sheets

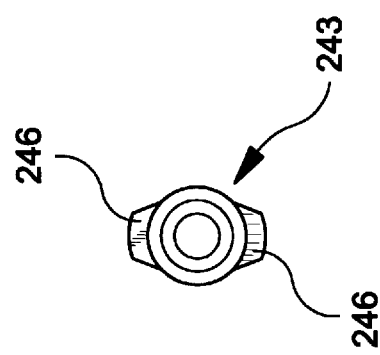
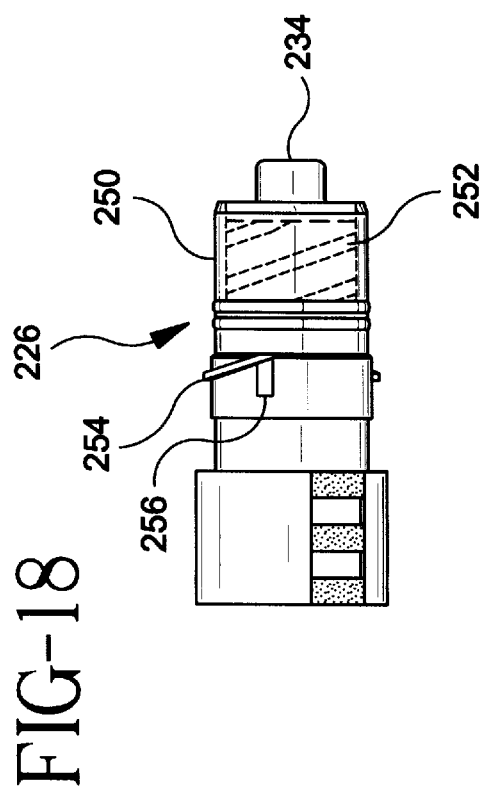
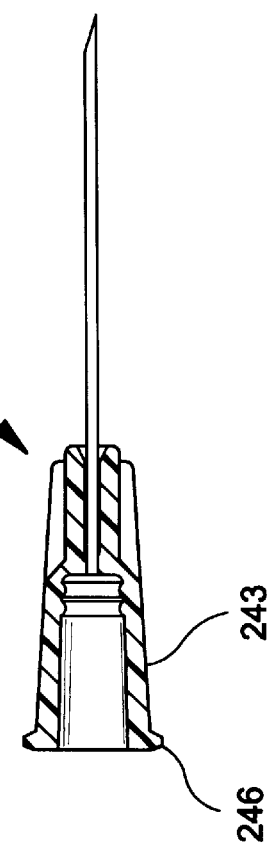

PRE-ASSEMBLED SYRINGE

FIELD OF THE INVENTION

The present invention is directed generally to a fluid dispensing syringe, and more particularly, directed to a medical syringe of the type having a fluid dispensing body and a removable cover which encloses a hypodermic needle or IV access system and which assures securement of the needle or IV access system to the body of the syringe upon removal of the cover.

BACKGROUND OF THE INVENTION

One well known technique for dispensing medicinal fluids is by use of a medical syringe. Syringes of this type commonly include a cylindrical barrel which accommodates the medicinal fluid, and a plunger which is movable within the barrel so as to dispense the fluid contained therein. The fluid is dispensed or injected through a hypodermic needle or IV access device. In certain types of syringes, the hypodermic needle or I.V. access device may be attached to the barrel by means of an injection holder supported by the barrel. In other types of syringes, the hypodermic needle may be directly affixed to the syringe, such as by a staked needle arrangement.

In many instances, the syringes are designed for single dosage. In these single dosage situations the medicinal fluid may be prefilled in the barrel of the syringe. Such a prefilled single-use syringe is provided with the hypodermic needle or IV access device attached to the injection holder or, in the case of a staked syringe, is directly affixed to the distal end of the syringe barrel. A safety cap or cover is placed over the syringe to enclose the needle or IV access device. The safety cap may be removed by the user so that the medicinal fluid contained within the barrel can be injected.

During assembly of the syringe, the injection member, namely the hypodermic needle or IV access device, may be frictionally attached to the injection holder by placing the injection member within the cover and then attaching the cap to the injection holder. In this manner, the injection member need not be directly handled. The attachment of the cover to the injection holder secures the injection member to the injection holder so that when the cover is removed, the injection member is retained on the injection holder for use. Alternatively, the needle or I.V. access device can be placed onto the injection holder, thereafter placing the cover over the needle or I.V. access device.

Prior to shipment of the assembled prefilled syringe, the syringe must undergo certain secondary operations. One of these secondary operations includes exposing the syringe to a sterilizing treatment, such as a steam treatment or an ethylene oxide (EtO) gas treatment. To assure that the steam or EtO gas completely envelops the entire syringe, especially the injection member, the cap is designed to be retained on the injection holder guide such that the sterilizing medium can penetrate beneath the cap and around the injection member. However, the temperature or pressure variations to which the syringe is subjected during such sterilization procedures, coupled with other forces during shipment and handling, may have a tendency to dislodge the injection member from its frictional securement with the injection holder. In addition, and particularly in the case of plastic components, such procedures may cause variations in the fit between the injection member and the injection holder. Thus, when the syringe is delivered to the user, and the cover is removed from the holder, it may be found that the injection member is not properly seated on the injection holder. This would require the user to re-secure the injection member to the syringe. This action may present a safety hazard and/or result in contamination of the sterilized surface of the injection member.

It is therefore desirable to provide a syringe assembly which assures the retentive frictional securement of the injection member to the injection holder prior to use.

SUMMARY OF THE INVENTION

The present invention provides a syringe assembly for dispensing a fluid of the type wherein an injection member is fitted onto an injection holder. The syringe assembly includes a hollow barrel having opposed open ends defining a fluid-containing chamber therebetween. A manually operable plunger is insertable into one end of the barrel for movement within the chamber. An injection holder is attached to the other end of the barrel. An injection member through which the fluid is dispensed is removably secured to the injection holder. A cover accommodates the injection member and is removably attachable to the injection holder. The cover is movable with respect to the injection holder from a first position, where the cover is retained on the injection holder, to a second position, where the cover is removed from the injection holder. Movement of the cover from the first position to the second position assures the removable securement of the injection member to the injection holder.

As more particularly described by the preferred embodiment herein, the cover and the injection holder include complimentary key and keyway structure which provides for the assembling of the cover onto the injection holder. The cover is movable in a manner whereupon removal of the cover from the injection holder, the injection member is repositioned with the injection holder so as to assure that the injection member is secured to the injection holder.

The keyway, which may be provided on the injection holder, is defined in one configuration by a tortuous channel. The key, which may be provided on the cover, includes a projection which rides within the channel. The channel defines a cam surface which is engagable with the projection. Other configurations of the complimentary keyway and key structure are possible.

The cover may be removably secured to the injection holder by rotative movement with respect thereto. Such rotative movement causes said injection member to be secured to the injection holder. Alternately, the cover may be removably secured to the injection holder by a push-twist-pull movement, such movement effecting secure positioning of the injection member to the injection holder. Of course, it will also be understood by the skilled artisan that the cover and/or injection holder can be designed such that other movements, such as a push-twist or twist-pull movement, are also possible.

BRIEF DESCRIPTION OF THE DRAWINGS

FIG. 18 depicts a needle holder adapted for use as a luer-lock syringe.

FIG. 19 depicts an injection device adapted for use with a luer lock syringe.

FIG. 20 is a top view of the injection device of FIG. 19.

DETAILED DESCRIPTION OF THE INVENTION

Figure 1:
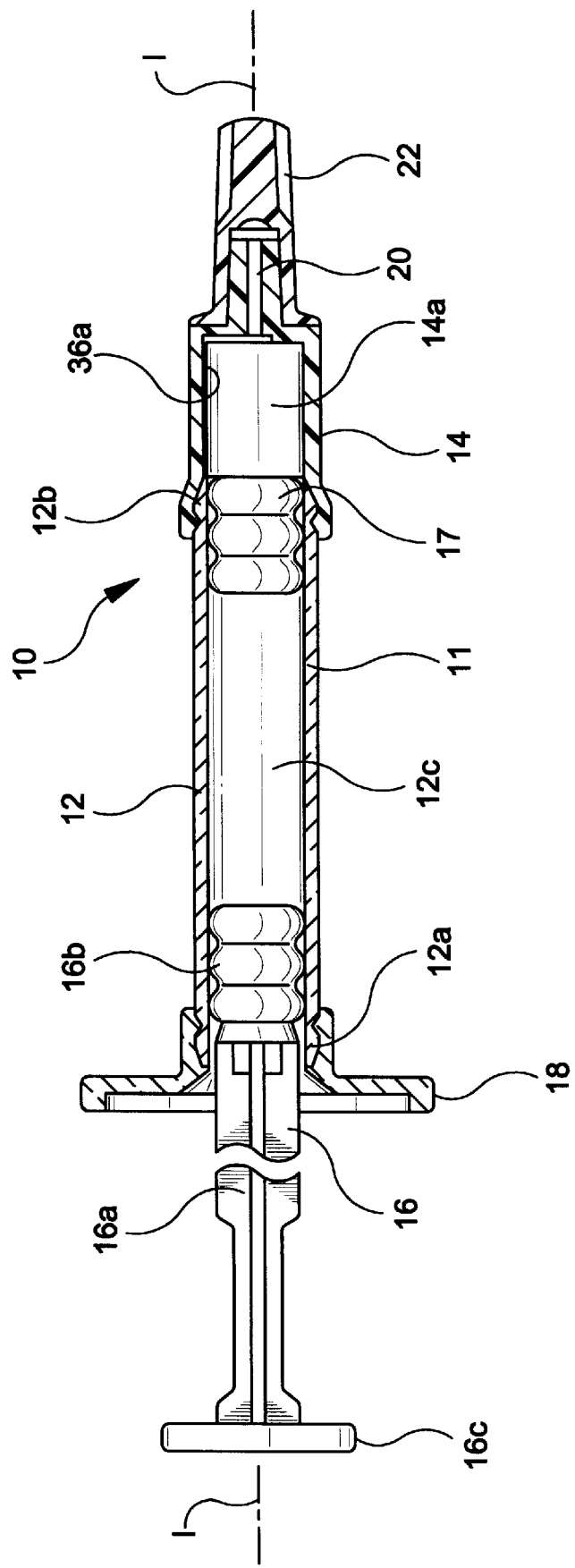
FIG. 1 is a longitudinal sectional view of a prior art syringe of the type which may be used in accordance with the present invention.

Referring to FIG. 1, a syringe assembly 10 of the type which may be used in accordance with the present invention is shown. The syringe assembly 10 shown in FIG. 1 is of the leur slip type more fully shown and described in U.S. Pat. No. 4,235,235 to Bekkering, issued Nov. 25, 1980, which is incorporated by reference herein for all purposes.

Syringe assembly 10 includes a prefillable sealed syringe 11 and a cover 22. Syringe 11 includes an elongate syringe body or barrel 12 extending along longitudinal axis "1" having an injection holder 14 sealingly secured to one end and a discharge plunger 16 insertable through the other end of the barrel 12. Cover 22 encloses an aperture 20 provided in injection holder 14. Barrel 12 is typically formed of glass or plastic. Cover 22, as well as injection holder 14, may also be formed of a suitable plastic. As is conventional in the syringe art, a hypodermic needle is typically a stainless steel hollow tube.

The syringe barrel 12 is generally an elongate cylindrical member having two opposed open ends 12a and 12b which define chamber 12c therebetween chamber 12c is designed to accommodate a dosage of a medicinal fluid for injection either directly or indirectly into a patient. One end 12a of barrel 12 accommodates discharge plunger 16 therein. Barrel end 12a may also support a laterally extending finger grip flange 18 which may be secured to or integrally formed therewith. Finger grip flange 18 is used in combination with discharge plunger 16 to facilitate handling as well as discharge and/or aspiration of the syringe. In this regard, discharge plunger 16 includes an elongate plunger rod 16a having an elastomeric piston 16b at one end and a thumb engaging flared portion 16c at the other end. Piston 16b, which may be formed of a pharmaceutical grade elastomer, effects a fluid-tight seal with the inner wall of barrel 12. In a manner well known in the syringe art, manual pushing and retraction of discharge plunger 16 within barrel 12 effects the discharge and aspiration functions of the syringe 11.

Syringe assembly 10 also includes a front piston 17, located within barrel 12 and spaced from piston 16b to enclose the medicament (not shown) which is prefilled within chamber 12c. Front piston 17 is initially placed adjacent open end 12b so as to retain, in a fluid tight manner, medicament held in chamber 12c. Upon the application of distal pressure on plunger 16, front piston 17 is forced into section 14a of injection holder 14 (illustrated in FIG. 1), with slot 36a (hereinafter described) permitting fluid flow past front piston 17 and out of needle 20.

Injection holder 14 is sealingly secured over end 12b of barrel 12 and is designed to mate with an injection member 27, as will be further described hereinbelow. Syringe assembly 10 further includes an elongate open-ended cap or cover 22 which is designed to surround the aperture 20 and a portion of the injection holder 14 so as to prevent contact with the aperture thereby assuring safety as well as sterility of the aperture during storage and transportation.

As previously described, one drawback in certain prior art syringes where an injection member is fitted to an injection holder is the ability to ensure that upon removal of the cover from the injection member, the injection member will be properly secured to the injection holder. The present invention addresses such drawbacks of the prior art syringes.

Figure 2:
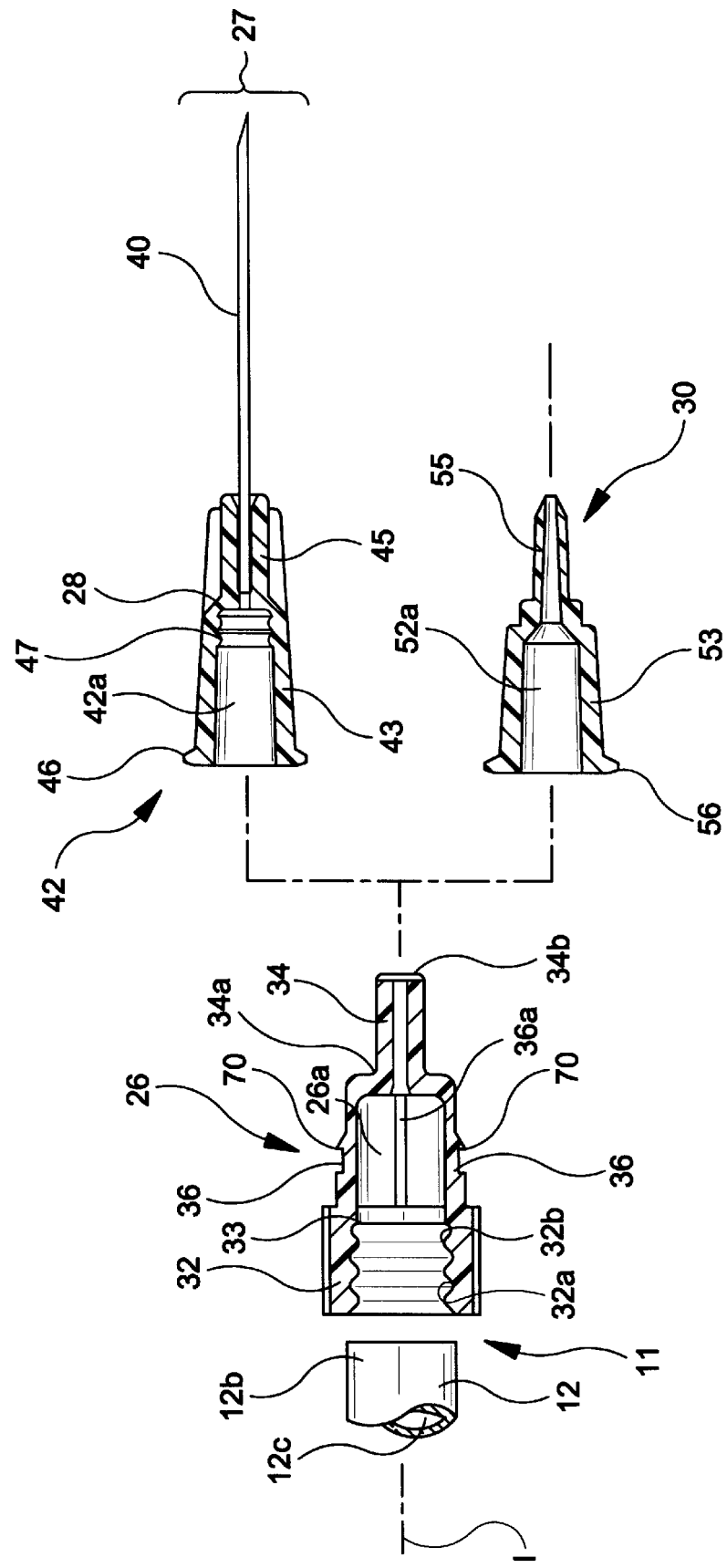
FIG. 2 is an exploded sectional view of components of an improved syringe assembly of the present invention, showing the alternate securement of a hypodermic needle assembly or an IV access device to an injection holder.

Referring then to FIG. 2, improvements in syringe assembly 10 in accordance with the present invention may now be described. The present invention provides an improved technique for securing a cover 24 (see, for instance, FIGS. 3 and 4) to an injection holder 26 so as to assure the attachment of an injection member 27 to the injection holder 26 upon removal of the cover 24 therefrom. The present invention also permits facile removal of the injection member from the injection holder subsequent to use of the device.

As used herein throughout, the term "injection member" is defined to include structures which facilitate the discharge of fluid from syringe 11 either directly into the patient percutaneously or into another injection system such as an IV access system. For example, as shown in FIG. 2, injection member 27 of the present invention may include either a hypodermic needle assembly 28 or an IV access device 30, either of which may be used with injection holder 26.

Figure 6:
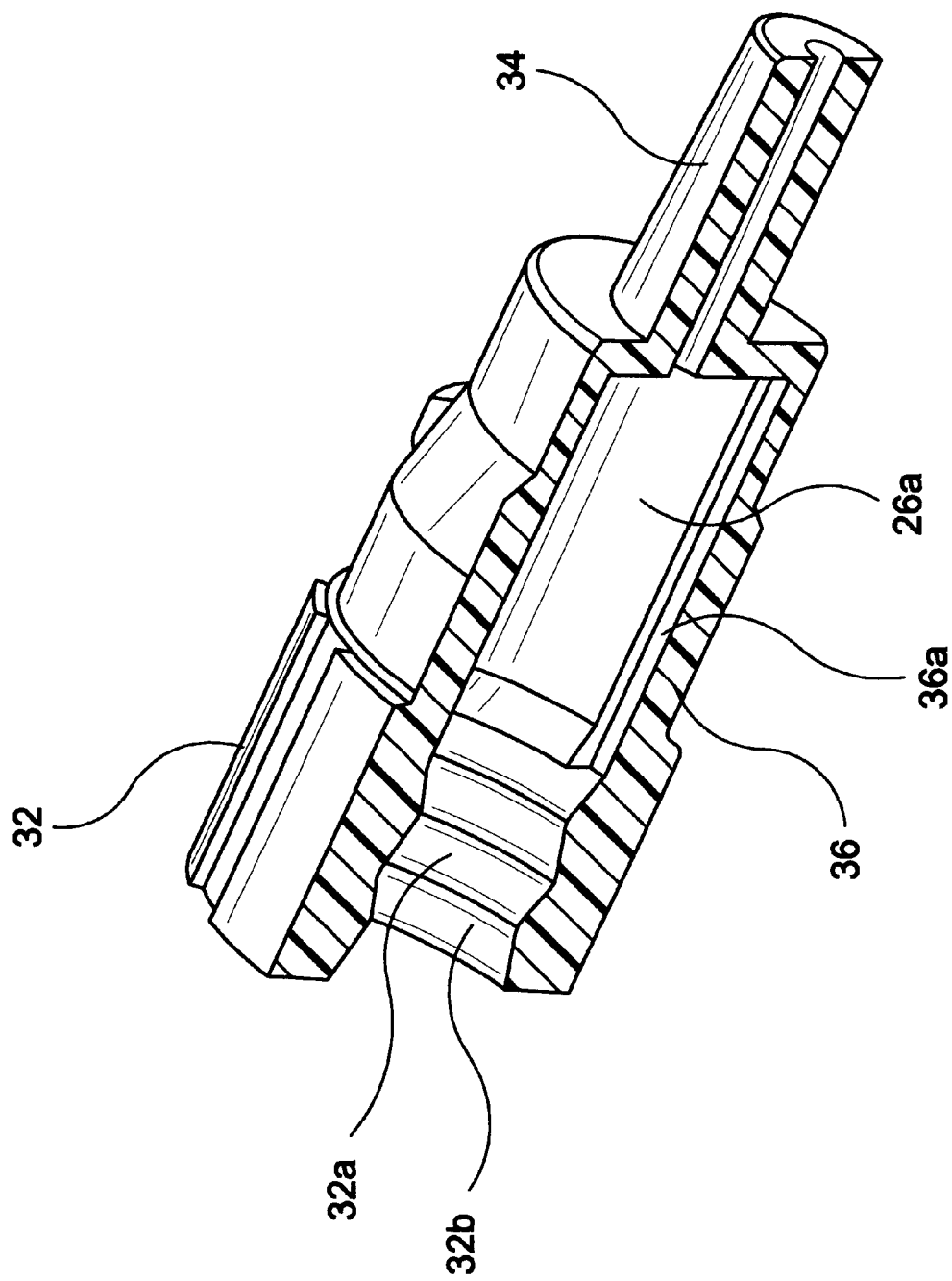
FIG. 6 is a perspective sectional showing of the injection holder of FIG. 5.
Figure 7:
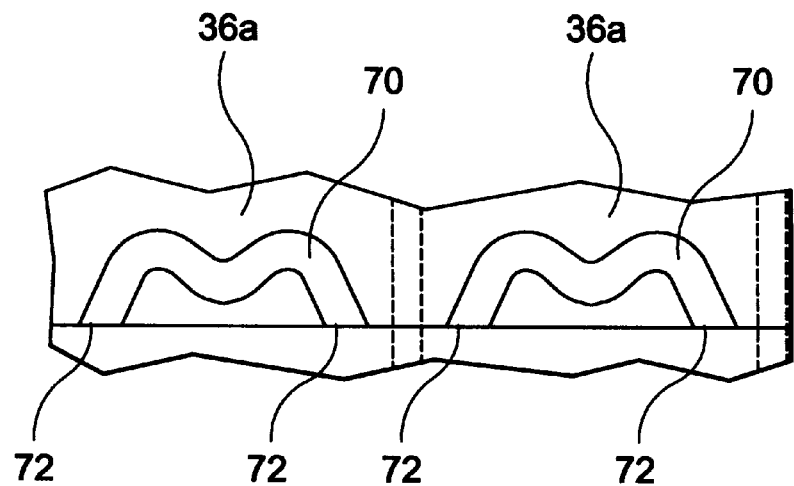
FIGS. 7 and 8 are schematic representations of keyway structure employed on the injection holder of FIG. 5.

Referring to FIGS. 2, 6, and 7, injection holder 26 of the present invention may be described. Injection holder 26 is an elongate, generally cylindrical member formed of a suitable plastic having a step wise transition between a cylindrical collar 32 at one end and a tapered neck 34 at the other end. A central shaft 36 between collar 32 and neck 34 effects such transition. Injection holder 26 includes an elongate bore 26a extending between and through collar 32 and neck 34. Bore 26a is designed to receive front piston 17 upon use of the syringe and to permit the dispensing of fluid therethrough.

An internal cylindrical wall 32a of collar 32 is provided with longitudinally spaced annular ridges 32b for frictional sealing engagement with end 12b of syringe barrel 12. The distal end of the syringe barrel 12 is designed to be seatingly supported by an internal shoulder 33 transitioning between collar 32 and shaft 36. The internal wall of shaft 36 further includes therein one or more elongate slots 36a therealong. Slot 36a, which is also shown in FIG. 1, facilitates dispensing of medicinal fluid around front piston 17 from chamber 12c of barrel 12 through injection holder 26.

Neck 34 of injection holder 26 is generally frustoconical in shape tapering from one end 34a adjacent shaft 36 to a distal end 34b. Neck 34 is designed to accommodate in frictional engagement injection member 27, which can be either hypodermic needle assembly 28 or IV access device 30. It will, of course, be understood to the skilled artisan that the injection member can comprise other constructions, such as blunt cannula formed of metals or plastics, or other means known for the transport of fluid to or from the barrel.

Injection member 27 may comprise a hypodermic needle assembly 28. Hypodermic needle assembly 28 includes needle support 42 which is formed of a suitable plastic. Needle support 42 is an elongate member having a hollow open frusto-conical mounting end or hub 43 for frictional securement to injection holder 26 and a needle accommodating end 45 for retaining a hypodermic needle 40. Needle support 42 includes a tapered central bore 42a extending from hub 43 to needle accommodating end 45. Needle support 42 is designed to be frictionally fitted over neck 34 of injection holder 26 with neck 34 extending into bore 42a thereof. The relative resiliency of the plastic material forming both needle support 42 and injection holder 26 permits such frictional securement therebetween. Hub 43 may also include an outwardly directed annular skirt 46 at the end thereof, the purpose of which will be described in further detail hereinbelow. It will be understood, of course, that annular skirt 46 may be substituted by wings, ridges, dots, or other structure as will become more evident hereinbelow.

Injection member 27 may also comprise an IV access device 30 formed of a suitable plastic. IV access device 30 is an elongate member having a generally hollow open frustoconical mounting end or hub 53 for frictional securement to injection holder 26 and a dispensing end 55. IV access device 30 includes a central bore 52a extending between hub 53 and dispensing end 55. Dispensing end 55 is designed for insertion into an IV access assembly (not shown) in a fashion which is conventional in the syringe art. The hub 53 of IV access device 30 is shaped similar to the hub 43 of needle support 42 described above, so as to insertably frictionally accommodate neck 34 of injection holder 26 therein. IV access device 30 also includes an annular skirt 56 adjacent the end of hub 53 which is substantially similar to skirt 46 of needle support 42.

Figure 3:
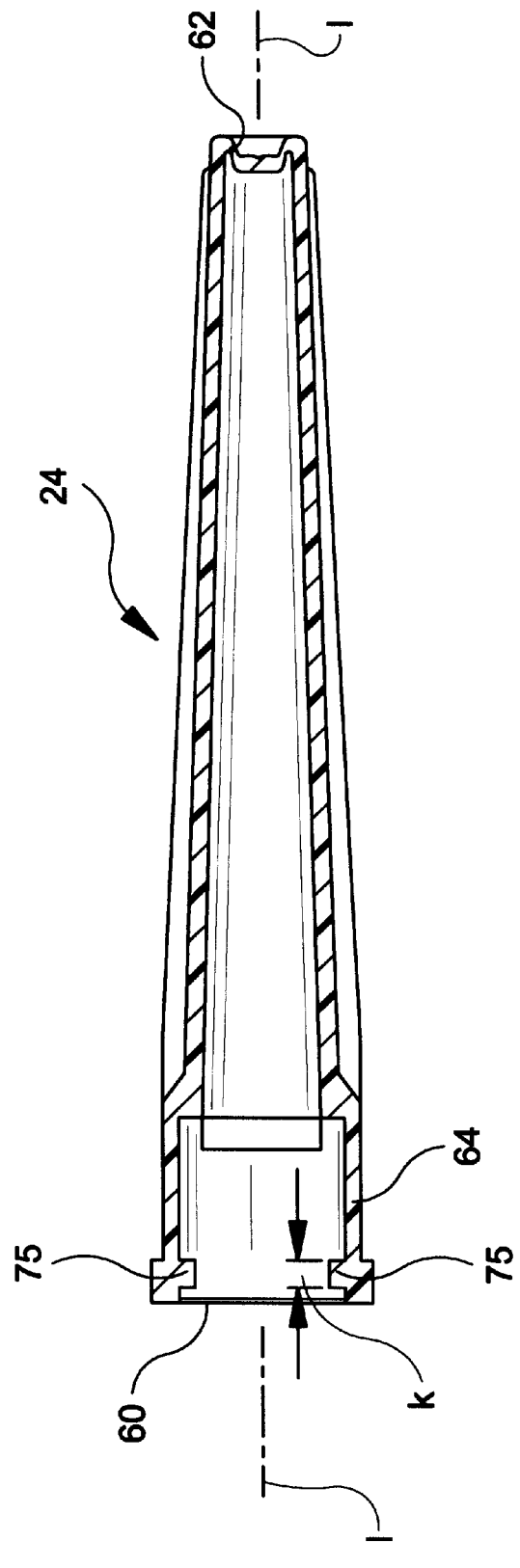
FIG. 3 is a longitudinal sectional showing of a cover which is used in combination with the syringe assembly of the present invention.
Figure 4:
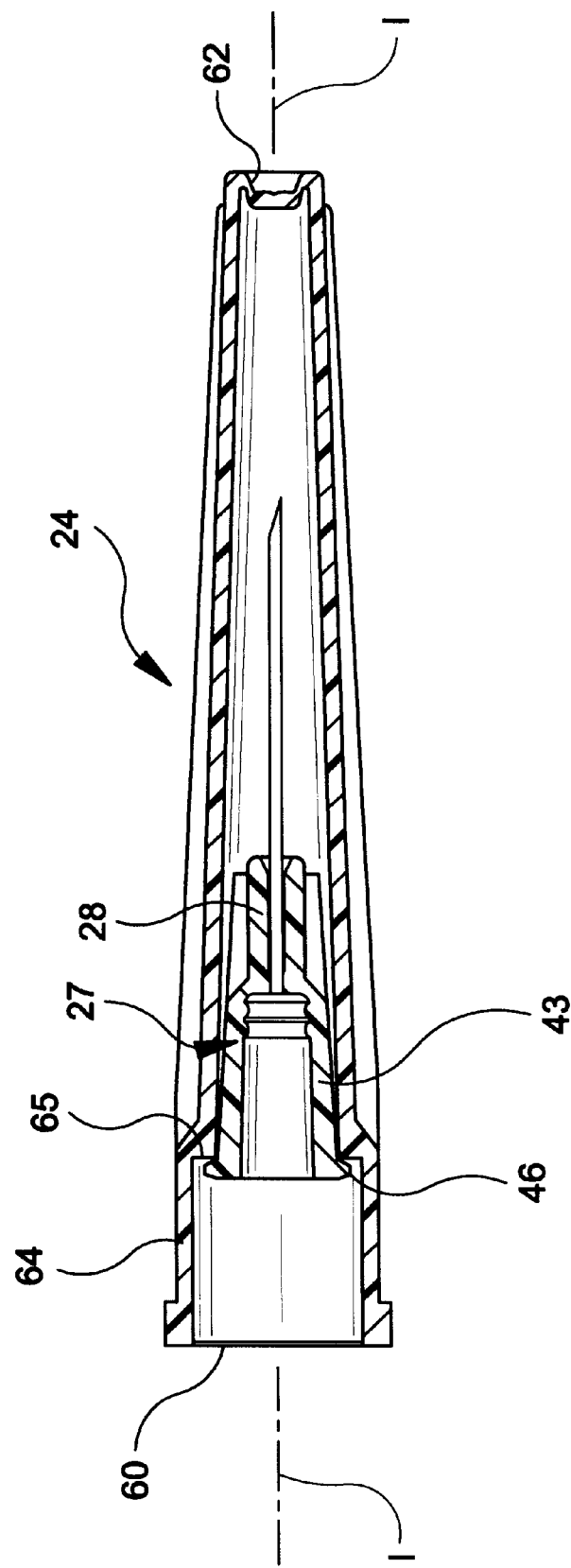
FIG. 4 is a longitudinal sectional showing of the cover of FIG. 3 showing the hypodermic needle assembly of FIG. 2 positioned therein.
Figure 5:
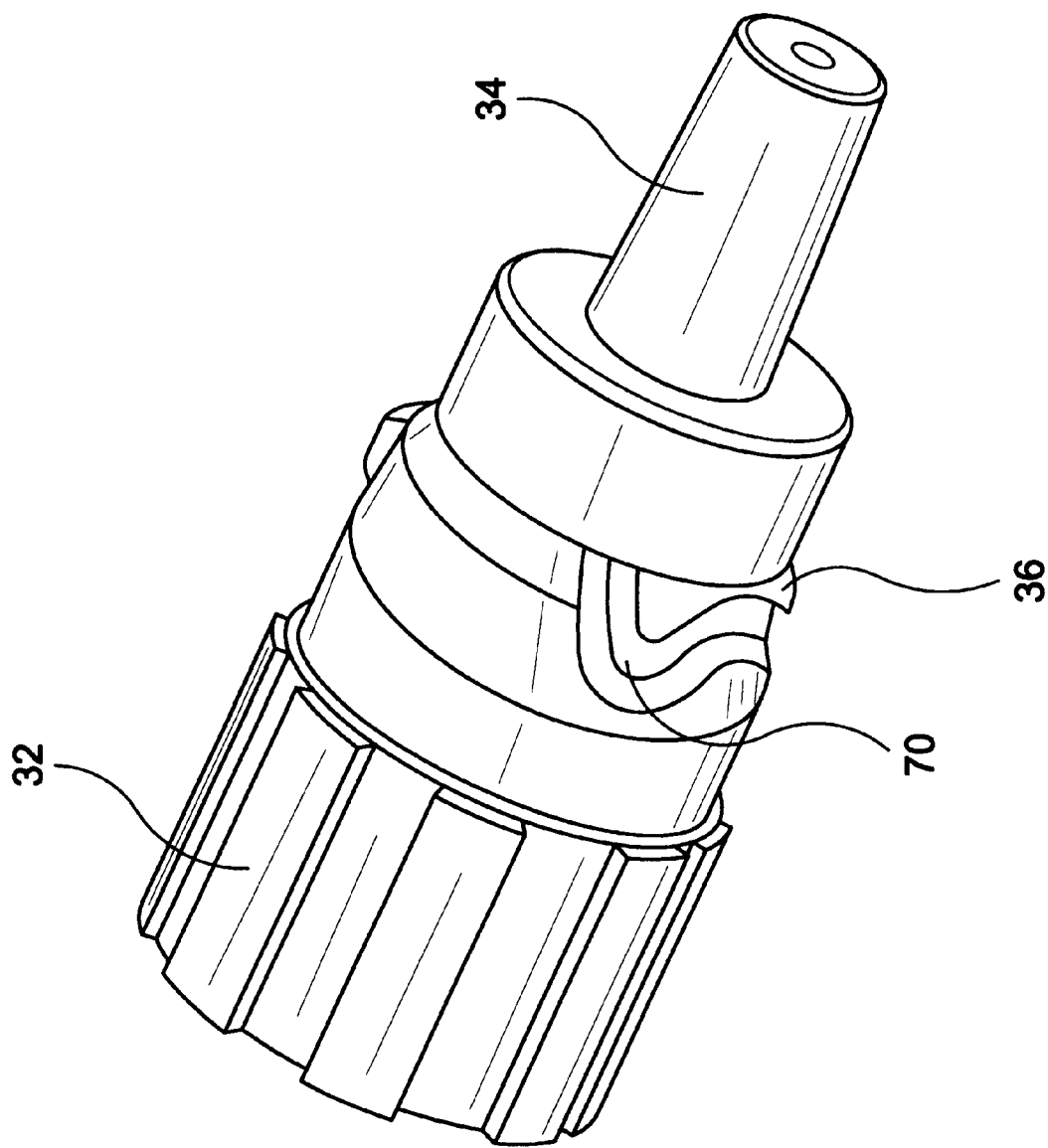
FIG. 5 is a perspective showing of injection holder of FIG. 2.

Referring now to FIGS. 3 and 4, cover 24 is an elongate generally frustoconical member also formed of a suitable plastic and includes an open end 60 and a closed end 62. Cover 24 is designed to accommodate injection member 27 of either type described above. Cover 24 also includes a generally cylindrical connection portion 64 adjacent open end 60, designed for removable securement to injection holder 26. As is known in the syringe art, cover 24 is designed to attach to injection holder 26 in a manner which fully encloses the injection member 27. Furthermore, as shown in FIG. 4, the cover 24 is designed to accommodate injection member 27 therein (in the FIG. 4 example, needle assembly 28) so that upon attachment of the cover to the injection holder 26, the hub 43 of needle assembly 28 is frictionally secured over neck 34 thereof.

In order to properly position needle assembly 28 on neck 34 of injection holder 26, cover 24 includes an inwardly directed shoulder 65 which forms a seating surface for skirt 46 of needle assembly 28. As will be described in further detail hereinbelow, the relative positioning of needle assembly 28 within cover 24 assures that when cover 24 is positioned over injection holder 26, hub 43 of needle assembly 28 will be frictionally secured to neck 34. Thus, the needle assembly 28 is attached to the injection holder 26 without need for the user to handle the needle assembly 28, thereby lessening the chances of an accidental needle stick or unsterile contact therewith.

As mentioned above, while attachment of the cover 24 to the injection holder 26 serves to secure the injection member 27 thereto, vibration and movement during shipping and handling or post assembly processing such as that which may be encountered during sterilizing treatments, may cause the injection member 27 to become dislodged from its seated position with the injection holder 26. The present invention provides a unique coupling of the cover 24 to the injection holder 26 to assure that the injection member 27 is properly positioned on the injection holder 26 upon removal of the cover therefrom.

Referring additionally to FIGS. 5–9, injection holder 26 and cover 24 include interconnection structure in the form of a complimentary key and keyway which provides for unique interconnection therebetween. In a preferred embodiment, an outer cylindrical wall 36a of shaft 36 includes a pair of diametrically opposed tortuous channels 70 thereon. The channels 70 are designed to accommodate therein a pair of diametrically opposed inwardly directed projections 75 (FIG. 3) adjacent the open end of cover 24. The width and depth of each channel 70 is selected to accommodate the projections 75. Projections 75 may be formed into any desired shape which may be readily accommodated within channel 70.

Projections 75 are designed to ride within one or more pairs of diametrically (ie, symmetrically) opposed tortuous channels 70 of shaft 36. The configuration of channels 70 allows rotative coupling of cover 24 to injection holder 26, such rotative coupling causing longitudinal movement of cover 24 with respect to the holder. The particular undulating configuration of tortuous channel 70 defines a plurality of spaced cam surface locations 80 and 82, which as will be described hereinbelow, provide for cammed movement of cover 24 with respect to injection holder 26.

Of course, it will be understood by the skilled artisan that in lieu of diametrically opposed channels and projections, a single channel and projection can be substituted. Alternately, two or more channels can be provided on outer cylindrical wall 36a that are asymmetrically located with respect to the cylindrical wall, these channels mated to similarly matched projections asymmetrically located about open end 60 of cover 24.

Figure 9:
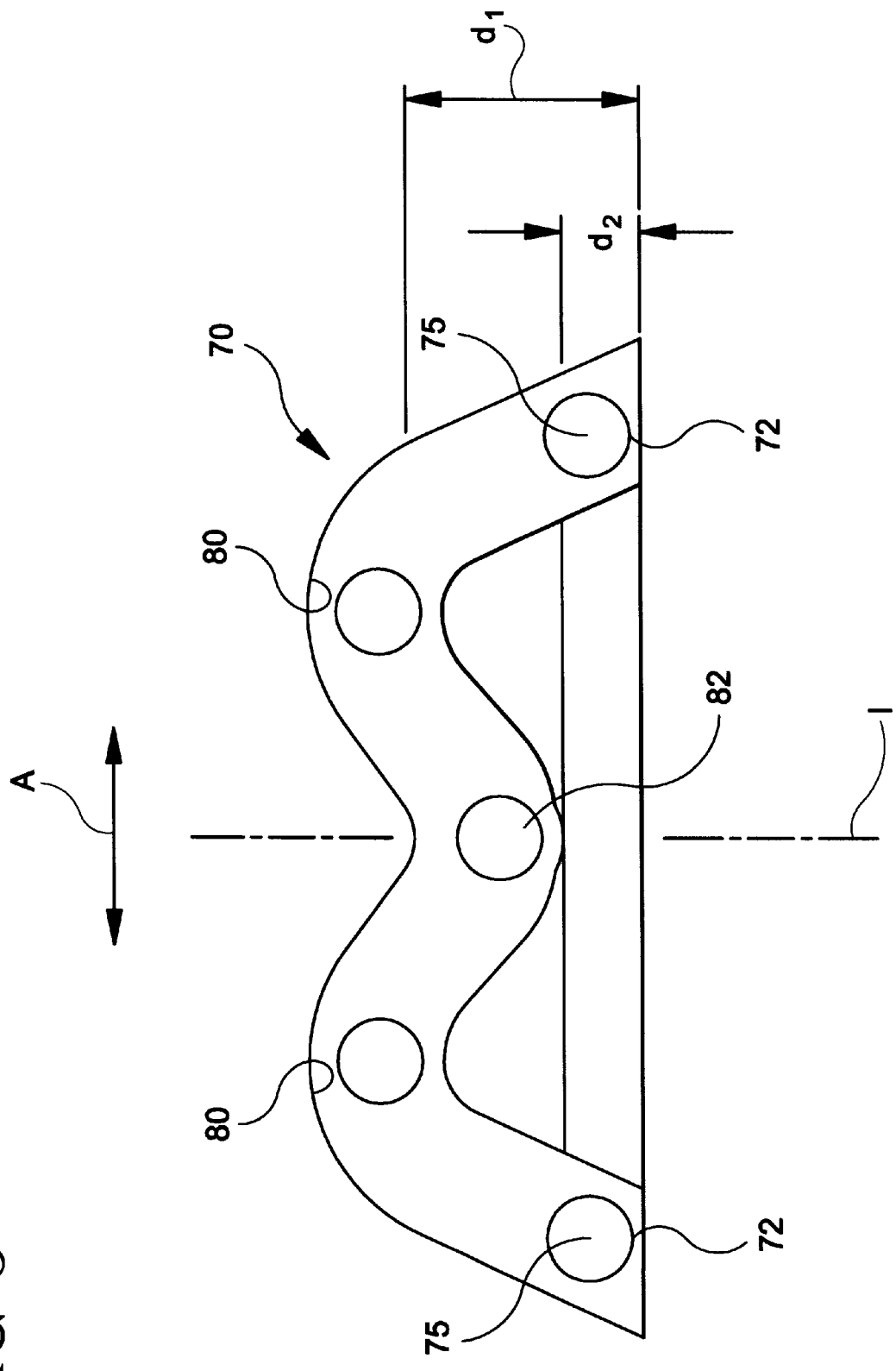
FIG. 9 is an enlarged schematic representation of the keyway structure of FIG. 7 showing progression of a projection of the cover of FIG. 3 therethrough.
Figure 10:
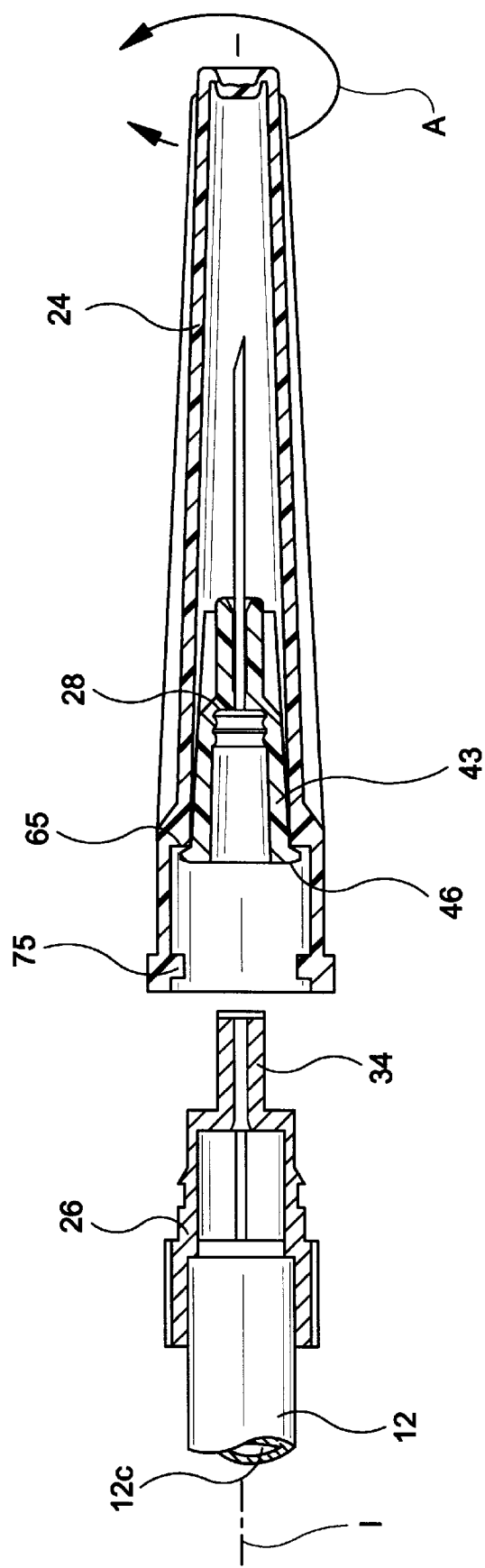
FIG. 10 is an exploded sectional view showing attachment of the cover to the injection holder.

Referring now to FIGS. 9 and 10, one manner for attaching cover 24 to injection holder 26 may be described. With respect to FIG. 10, cover 24 is shown supporting injection member 27 of the type comprising hypodermic needle assembly 28. It may be appreciated that injection member 27 of the type comprising IV access device 30 of FIG. 2 may also be employed.

Hypodermic needle assembly 28 may be positioned within cover 24 such that skirt 46 is seated on a shoulder 65. Of course, as previously mentioned, skirt 46 can be substituted by wings, edges, dots, or other structure allowing support of the hypodermic needle assembly to the cover.

This positions the hypodermic needle assembly 28 in proper position with respect to projections 75 of cover 24 so that upon positioning of projections 75 within channels 70 in a manner described hereinbelow, the hub 43 of hypodermic needle assembly 28 will be frictionally secured over neck 34 of injection holder 26.

Cover 24 is brought down onto injection holder 26 along longitudinal axis "1". Cover 24 is positioned so that diametrically opposed projections 75 enter each channel 70 through one of two entry openings 72 at each end of each channel 70. The projections 75 may be placed in either of the two entry openings 72 of each channel 70. As shown in FIG. 9, for completeness of description, projections 75 are shown positioned initially in both of entry openings 72 of channel 70. Continued movement of cover 24 effects both longitudinal movement (along axis "1"), as well as relative rotational movement, of cover 24. with respect to injection member 26. Such rotational movement, indicated by arrow A in FIGS. 9 and 10, may be either in the relative clockwise or counter-clockwise direction. depending upon into which of entry openings 72 projections 75 have been inserted.

Cover 24 is progressed both rotationally and axially to a position where each projection 75 is cammed to reside adjacent a first cam surface location 80 which is spaced a longitudinal distance $d_1$ from entry opening 72. The longitudinal distance $d_1$ through which cover 24 moves is sufficient to move the hypodermic needle assembly 28 carried thereby, from an unseated position to a seated position on neck 34 of injection holder 26. Thus, upon projections 75 traversing from entry opening 72 to first cam surface location 80, hub 43 of hypodermic needle assembly 28 is frictionally seated over neck 34 of injection holder 26.

After projections 75 have been located at first cam surface location 80, continued movement of cover 24 with respect to injection holder 26 causes continued rotational movement of cover 24 with respect to injection holder 26 as well as reverse longitudinal movement of cover 24 with respect injection holder 26. Projection 75 is thus cammed to reside adjacent a second cam surface location 82 which is spaced a longitudinal distance $d_2$ (which is less than $d_1$) from first cam surface location 80. In this position, cover 24 is captively retained on injection holder 26 by positioning projection 75 at second cam surface location 82. As hypodermic needle assembly 28 has already been frictionally fitted over neck 34 of injection holder 26, movement of cover 24 from a position where projection 75 resides adjacent first cam surface location 80 to a retracted position where projection 75 resides adjacent second cam surface location 82 does not disturb the frictional fit between hypodermic needle assembly 28 and injection member 26. All told, the movement of cover 24 from an unattached position to an attached position is effected by a rotative motion with the projection 75 being guided by residence within channel 70.

It will be apparent to the skilled artisan that alternate methods for attaching cover 24 to injection holder 26 may be effected. For instance, rather than first placing hypodermic needle assembly 28 in cover 24, the hypodermic needle assembly may be first positioned onto neck 34 of injection holder 26 in its seated position. Thereafter, cover 24 may be inserted over needle assembly 28, projection 75 entering channel 70 and being; rotated to the second cam surface position 82 without disturbing placement of needle assembly 28 with respect to neck 34. When cover 24 has been rotated to the second cam surface position, shoulder 65 of cover 24 maintains proper positioning of the needle assembly with respect to neck 34 of the injection holder.

With cover 24 thus retained on injection member 26, the entire syringe assembly 10 may be stored, handled, transported or subject to secondary operations such as sterilization procedures. During such procedures, vibratory forces or pressure or temperature variations may cause dislodgement of, or variations in the fit between, hypodermic needle assembly 28 from a frictionally seated position on neck 34 of injection member 26. The present invention provides for and assures the frictional repositioning of hypodermic needle assembly 28 on neck 34 of injection holder 26 upon removal of cover 24 therefrom.

In order to remove cover 24 from injection holder 26, cover 24 may be rotated in either the clockwise or counter-clockwise direction (arrow A). Such rotative movement causes projection 75 to move both rotationally and longitudinally from its position at second cam surface location 82 which is defined as an initial retention or storage location to a position wherein projection 75 resides adjacent first cam surface location 80 defined as a securement location. The repositioning of cover 24 (and, hence, movement of projection 75) a distance d1-d2 causes hub 43 to be repositioned onto neck 34 of injection holder 26. At this position, as cover 24 is moved back the longitudinal distance $d_1$ from its initial entry position adjacent opening entry 72, the repositioning of cover 24 will force hub 43 of hypodermic needle assembly 28 back onto neck 34 of injection holder 26. Continued rotation and axial movement of cover 24 causes projection 75 to withdraw to entry opening 72, which now serves as an exit opening so as to permit cover 24 to be removed from injection holder 26. The removal of cover 24 from injection holder 26 is thus effected by a simple rotative movement. Upon such removal, the hypodermic needle assembly 28 will be positioned in frictional securement over neck 34 for use.

Thus, during use of the syringe assembly 10 of the present invention, the cover 24 is both rotatively and axially movable with respect to injection holder 26 so that the cover is moved from a first position where the cover is retained on injection holder 26 and projection 75 is resident within channel 70 adjacent second cam surface location 82, to a second position where the cover removed from injection holder 26 by passage of projectior 75 through the exit/entry opening 72. However, in order to traverse from this first position to the second position, projection 75 of cover 24 must traverse through a third position defined at first cam surface location 80 where the hub 43 of hypodermic needle assembly 28 is frictionally reattached to neck 34 of injection holder 26. Thus, the removal of the cover 24 from the injection member 26 by the user repositions or assures the positioning of injection member 27 thereon.

Figure 8:
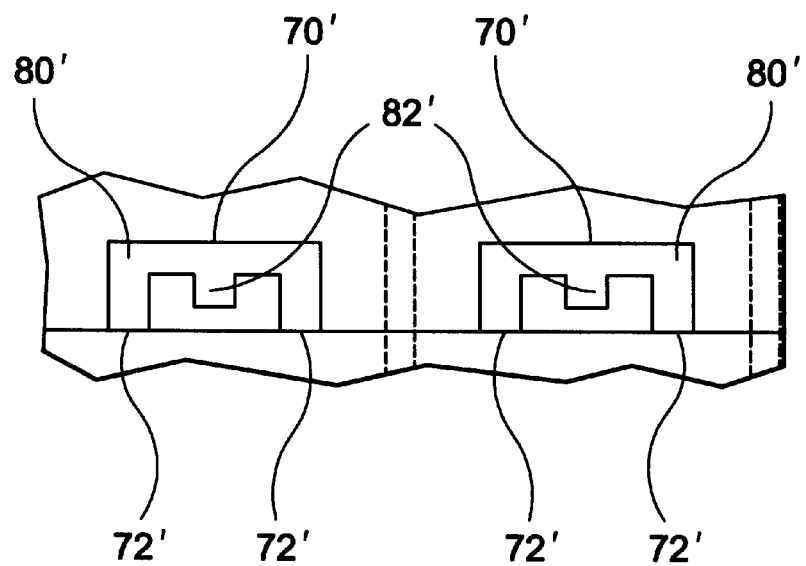

The particular shape of the tortuous channel 70 formed in shaft 36 of injection holder 26, as shown in FIG. 7, is one example. Other configurations are also within the contemplation of the present invention. In another example, as shown in FIG. 8, a tortuous channel 70' is formed in a shape which is segmented rather than curved, with assembly or disassembly effected by a push-twist-pull motion. As with the embodiment of FIG. 7, channel 70' includes a pair of entry (exit) openings 72', a first cam surface location 80', and a second cam surface location 82'. To assemble, projection 75 is pushed through an opening 72' towards first cam surface location 80', then twisted either clockwise or counter-clockwise and then pulled down into second cam surface location 82'. Removal is effected by the reverse push-twist-pull motion. Here then, rather than a rotative motion with the embodiment of FIG. 7, the movement of cover 24 from an unattached position to an attached position is effected by a push-twist-pull motion, with the projection 75 being guided by residence within channel 70'. Other configurations are also within the contemplation of the present invention.

Figure 11:
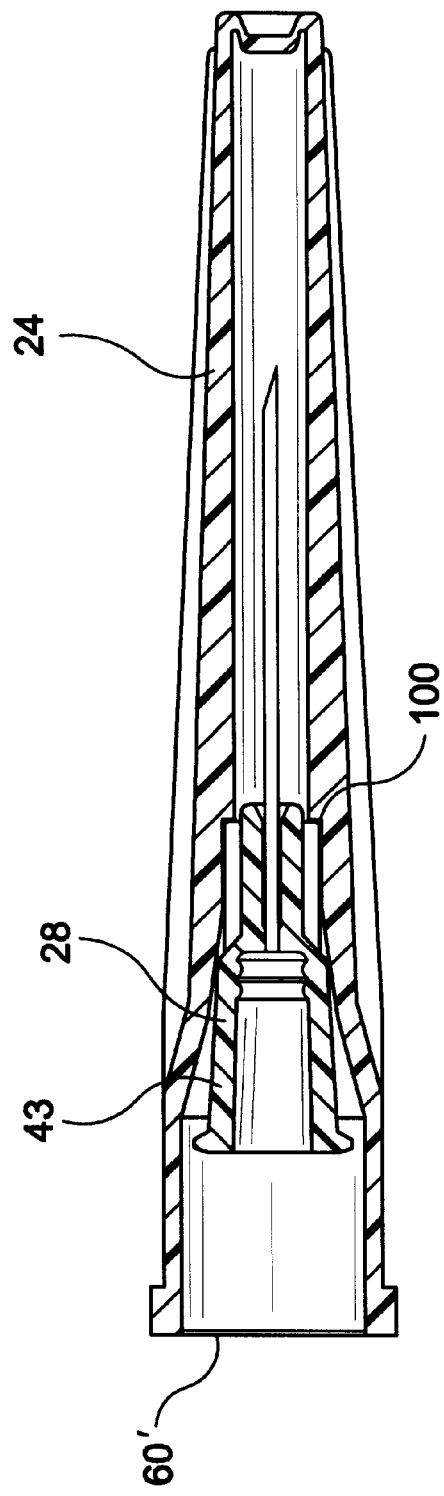
FIG. 11 depicts an alternate way to structure the needle cover for retention of the injection member.
Figure 12:
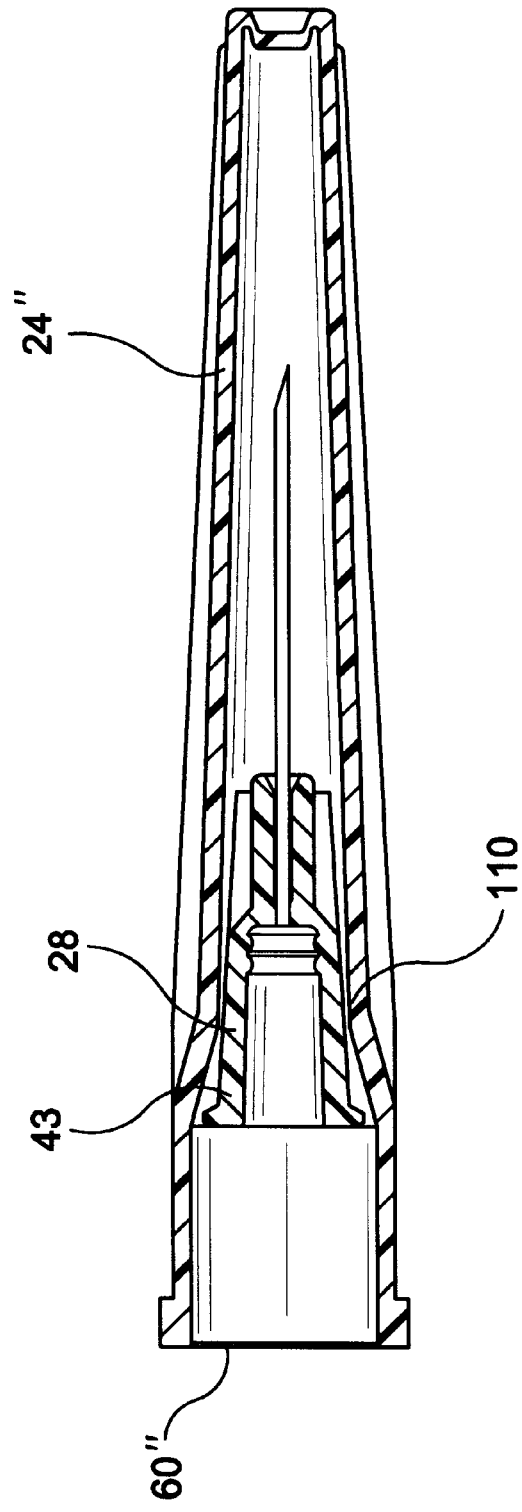
FIG. 12 depicts yet another way to structure the needle cover for retention of the injection member.
Figure 13:
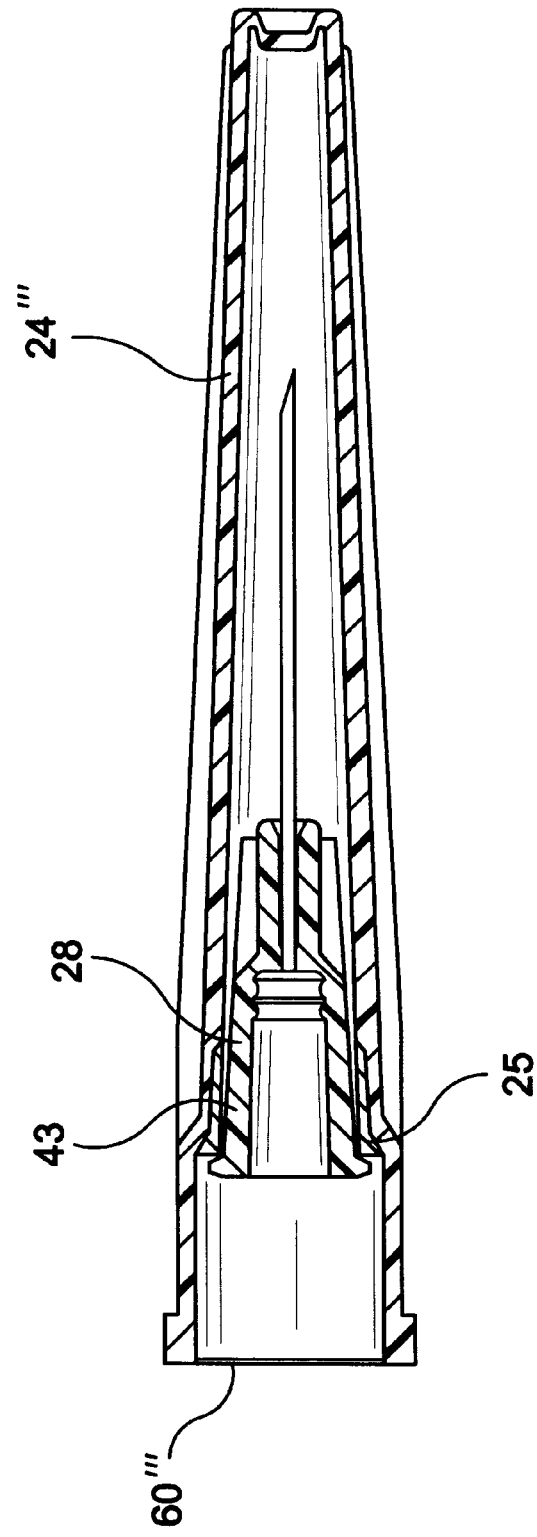
FIG. 13 depicts an insert member which may be inserted into the needle cover for retention of the injection member.

It may also be appreciated from the above description that in order to properly effect reseating of injection member 27 on injection holder 26, cover 24 must support the injection member at a fixed spacing with respect to the open end thereof The support of skirt 46 of hub 43 on shoulder 65 of cover 24 as shown in FIGS. 4 and 10 is one technique to assure proper spacing. However, other techniques are also within the contemplation of the present invention. For instance, referring to FIGS. 11–13, other examples of properly spacing hypodermic needle assembly 28 with respect to the open end of cover 24 may be shown. In FIGS. 11 and 12, the internal walls of covers 24' and 24" may be modified so as to retain hypodermic needle assembly 28 at proper position with respect to the open end 60',60" of the cover 24',24" (FIG. 11 illustrating a nub 100 provided to interact with hub 43 adjacent needle accommodating end 45, and FIG. 12 showing a nub 110 interacting with a portion of hub 43 intermediate the needle accommodating end and skirt 46). Further, in FIG. 13 a separate insert member 25 may be inserted into the open end 60''' of a further modified cover 24'''. Insert 25 can be formed from an elastomeric material, from metallic or plastic springs, or other the like. The insert 25 forms a seating platform for hypodermic needle assembly 28, maintaining its proper spacing from the open end 60''' of cover 24'''. Insert 25 can also serve to compensate for molding variations between the parts. Also, depending on the material and properties chosen for insert 25, the insert can serve to regulate or otherwise evenly distribute forces that are applied to hub 43 during the repositioning operation. With respect to each of the embodiments set forth above, proper securement of hub 43 of needle assembly 28 is assured by supporting the hub 43 at a position where movement of the hub a distance equal to $d_1 - d_2$ is sufficient to reseat the hub at a seated position with respect to the holder 26. A further advantage of insert 25 is that it can assist in easy removal of cover 24 from holder 26, by compensating for any alignment or molding variations or other deviations between holder 26, cover 24 and hub 43 that would interfere with easy opening of the cover. For instance, insert 25 can be formed from an elastic or resilient material which can compensate for the dimensional variations previously described.

Furthermore, the arrangement of the interfitting key and keyway structure of projection 75 within channel 70 is shown in the preferred embodiment (FIGS. 2 and 3) with the projection 75 being included adjacent the open end 60 of cover 24 and the channels 70 being positioned on the shaft 36 of injection member 26. However, it is within the contemplation of the present invention that the opposite arrangement may also be employed. Cover 24 may include diametrically opposed channels, such as those shown in FIGS. 7 and 8, on the internal wall thereof adjacent opening 60. Shaft 36 of injection member 26 may then include diametrically opposed projections for interfitting engagement within the channels of the cover. Of course, as described earlier, a single projection and channel may be provided, and in the case of two or more channels or projections, those channels and projections need not be diametrically opposed but can be asymmetrically provided on the cover and shaft, respectively.

Figure 14:
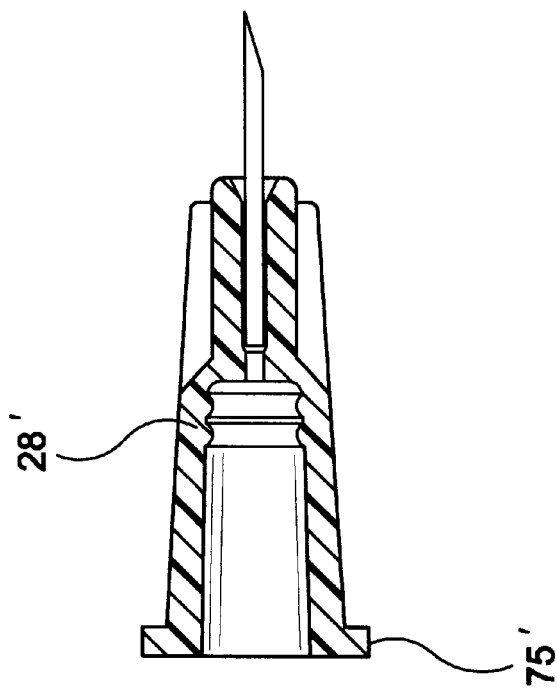
FIG. 14 illustrates providing projections on a hypodermic needle assembly.
Figure 15:
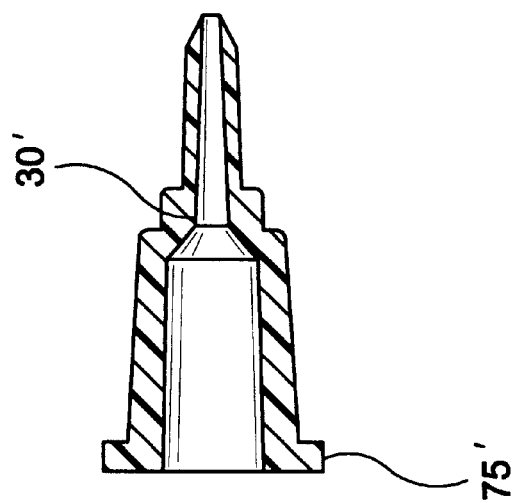
FIG. 15 illustrates providing projections on an I.V. access device.
Figure 16A:
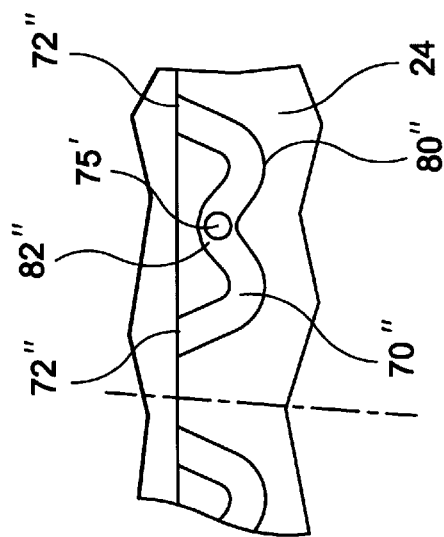
FIG. 16, 16A and 16B illustrates providing channels on an interior portion of the needle cover, for mating with the projections provided on the hypodermic needle or I.V. access device of FIGS. 14 and 15, respectively.
Figure 16B:
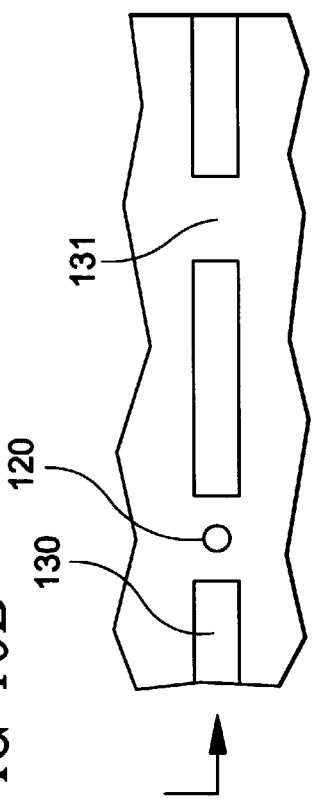
Figure 16:
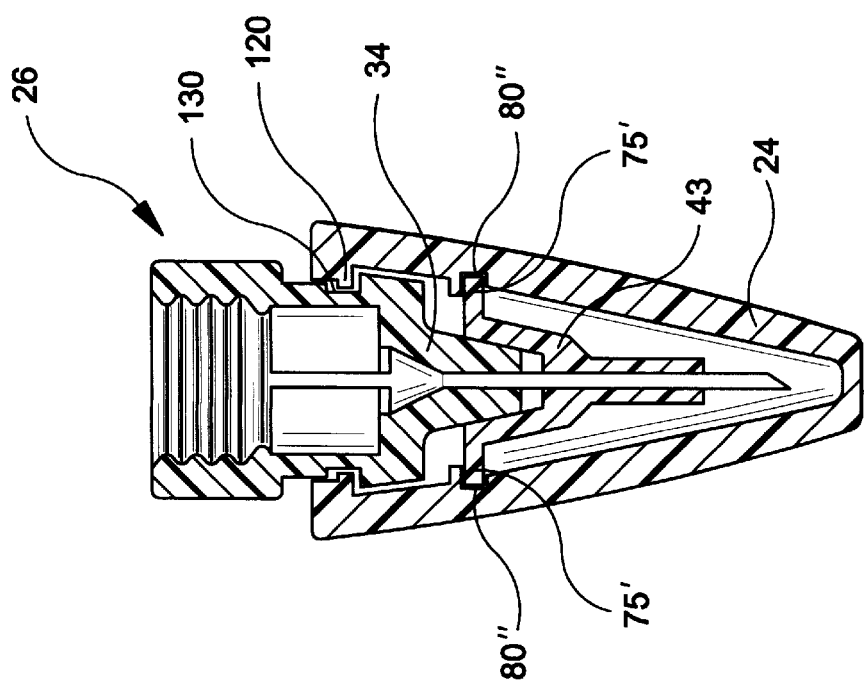
Figure 17:
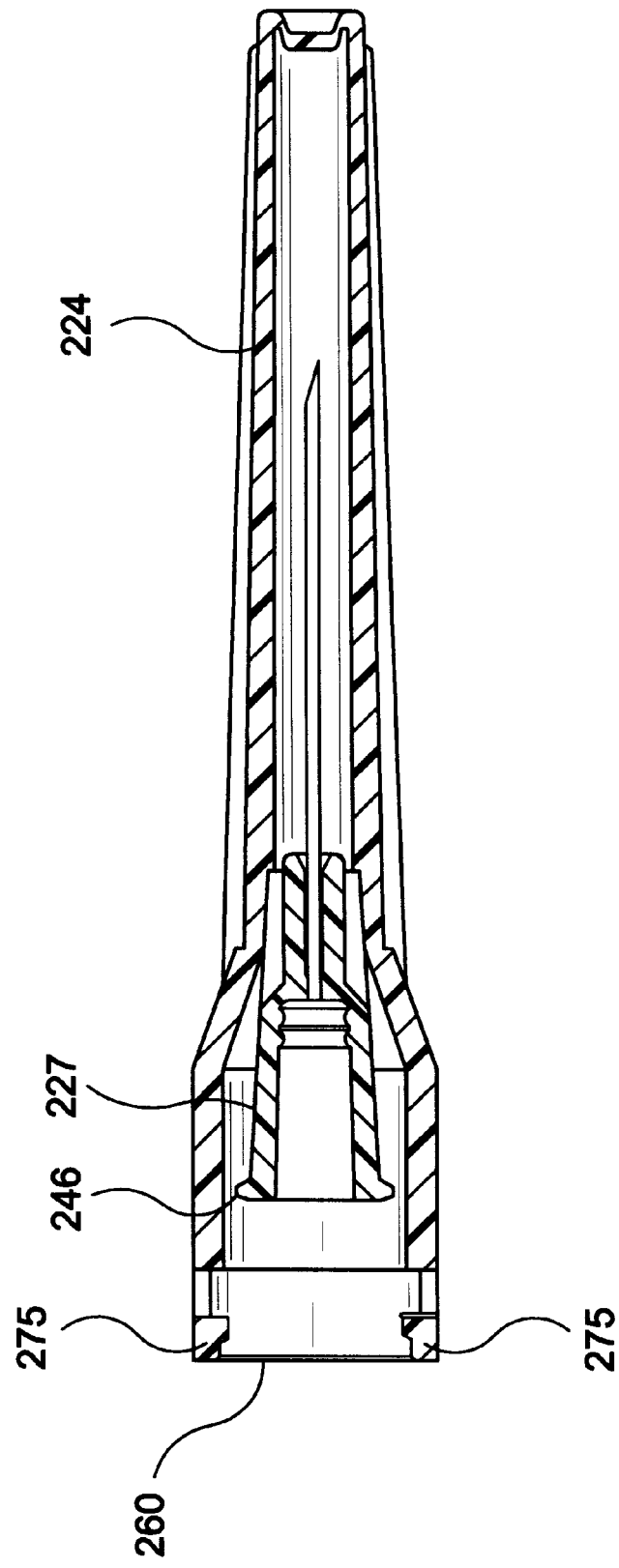
FIG. 17 illustrates an injection device placed in a needle cover for an arrangement of the invention adapted for a luer-lock syringe.
Figure 21:
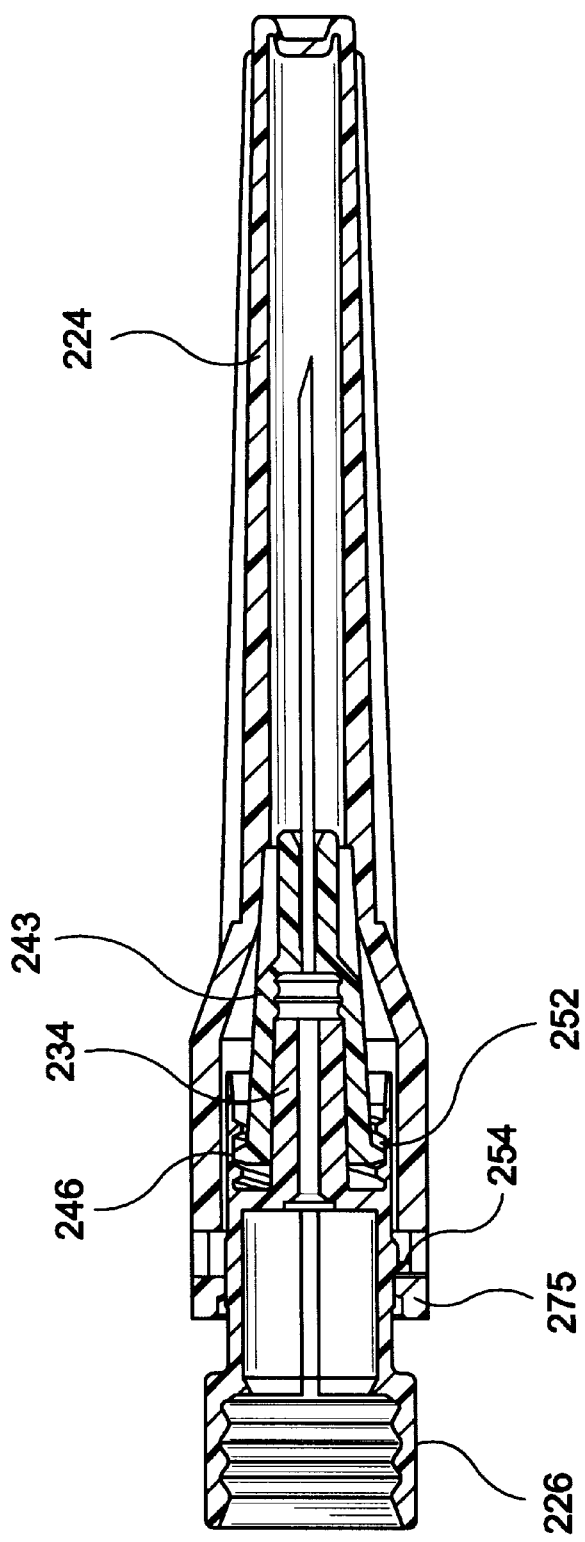
FIG. 21 illustrates placement of the needle cover and injection device onto a needle holder, adapted for use as a luer-lock syringe.

FIGS. 14–16 illustrate that it is also contemplated that the projections may be included on the injection member. Those projections are accommodated within channels formed on an interior portion of cover 24. As shown in FIG. 14, hypodermic needle assembly 28' includes opposed projections 75' in place of skirt 46. The projections 75' would become resident within channels 70" provided on an interior portion of cover 24 as illustrated in FIG. 1. Similarly, in FIG. 15, IV access device 30' is shown with diametrically opposed projections 75" in place of skirt 56. In this arrangement, injection member 27 is loosely held within cover 24, the projections 75" (75") resting within channels 70". Cover 24 is clipped onto holder 26 by means of a complementary projection and spacings arrangement 130, 120, which is releasable by the user. As illustrated in FIG. 16b. Rotation of cover 24 about holder 26 causes the projections 75' (75") of injection member 27 to follow channel 70". Injection member 27 will travel within cover 24 such that hub 43 is secured to neck 34 as previously described. Continued rotation of cover 24 about holder 26 causes projection 75' (75") to travel from second cam position 82" to first cam position 80" and then out exit openings 72". In this way, the projections 120 pass through the spacing 131 between projections 130, and upon rotation of the cover, the projections 120 move and are retained in place by projections 130 to prevent removal of the cover. The user may thereafter pull the cover from the holder, with the injection member secured to the holder.

Lastly, while a frictional fit of the hub 43 of injection member 27 with respect to neck 34 is shown, other mechanical securement combinations may be employed. For example, the engagement between injection holder 26 and injection member 27 may be by a common connection assembly referred to as a "Luer Lock".

FIGS. 17–21 illustrate the adaptation of the principles of the foregoing invention to such a Luer-Lock syringe. Injection device 227 includes a hub 243 having a pair of luer wings 246 adjacent the open end of the hub. Needle holder 226 is configured for mating action with such an injection device 227. Needle holder 226 includes a neck 234 which projects from a luer collar 250 formed at the distal end of the needle holder 226. Luer collar 250 includes an internal thread 252 designed to mate with luer wings 246 of hub 243. Needle holder 226 also features an outside thread 254, and an external detent 256 which interacts with cover 224.

Cover 224 includes a pair of projections 275 adjacent open proximal end 260. Injection device 227 is initially placed within the cover such that luer wings 246 are aligned with projections 275. It will be understood that the structure for retaining injection device: 227 within cover 224 may be that previously described.

Next, cover 224 and injection device 227 are screwed onto needle holder 226. Luer wings 246 of the injection device mate with internal thread 252 of the luer collar while projections 275 of the cover mate with external thread 254 of the needle holder. Thus, the screwing motion of the cover onto the needle holder securely affixes the hub to the neck. Projections 275 are locked in place by external detent 256, such that cover 224 cannot be removed other than by continuing to twist the cover in the direction of thread 254.

To remove the cover from the needle holder, a user must twist the cover in the direction of thread 254. This causes cover 224 to become dislodged from thread 254, permitting a user to remove the cover from needle holder 226. At the same time, cover 224 will reposition injection device 227 onto needle holder 226, should same have become dislodged from the holder, as previously described.

Other advantages of the invention are also readily apparent. For instance, by ensuring that the injection member is secured to the needle holder, a user can easily remove the cover to expose the needle for a desired use. Sometimes, it is desired to change the injection member during fill use of the syringe. For instance, where a drug prefilled into the syringe is to be reconstituted with a liquid, it is necessary to change the injector member after reconstitution so as to present a fresh injection member to administer the drug to a patient. The present invention permits a user to easily change the injection member, a use always being sure that the injection member is attached to the injection holder and not located within the cover upon removing the cover form the holder.

Various changes to the foregoing described and shown structures would now be evident to those skilled in the art. Accordingly, the particularly disclosed scope of the invention is set forth in the following claims.

What is claimed is:

1. A syringe assembly for dispensing a fluid comprising:
    a hollow barrel having opposed open ends defining a fluid-containing chamber therebetween;
    a manually operable plunger insertable in one end of said barrel for movement within said chamber;
    an injection holder attached to said other end of said barrel;
    an injection member through which said fluid is dispensed in response to said movement of said plunger, said injection member being removably secured over a portion of said injection holder; and
    a cover for accommodating said injection member and being removably attachable to said injection holder, said cover being movable with respect to said injection holder from a first position where said cover is retained on said injection holder to a second position where said cover is removed from said injection holder and wherein movement of said cover from said first position to said second position assures said removable securement of said injection member to said injection holder,
    wherein said cover and said injection holder include interfitting key and keyway structure for guiding movement of said cover between said first and second positions.

2. A syringe assembly of claim 1 wherein:
    said injection member is positionable within said cover for movement therewith with respect to said injection holder.

3. A syringe assembly of claim 2 wherein said movement of said cover from said first position to said second position is effected by movement of said cover in a first direction towards said one end of said barrel and subsequent movement of said cover in a second direction opposite said first direction.

4. A syringe assembly of claim 3 wherein said cover is attachable to said injection holder by movement of said cover from said second position to said first position.

5. A syringe assembly of claim 4 wherein one of said cover and said injection holder includes said key structure and the other of said cover and said injection holder includes said keyway structure.

6. A syringe assembly of claim 5 wherein said key structure includes an extending projection and wherein said keyway structure includes a tortuous channel, said projection being movable within said channel.

7. A syringe assembly of claim 6 wherein said channel includes an exit/entry opening location for insertion and removal of said projection and defining said second position.

8. A syringe assembly of claim 7 wherein said channel includes a retention location spaced from said exit/entry opening location for accommodating said projection and defining said first position.

9. A syringe assembly of claim 8 wherein said retention location is positioned more proximate said one end of said barrel then said exit/entry opening location.

10. A syringe assembly of claim 9 wherein said channel includes an injection member securement location spaced from said exit/entry opening location and said retention location, said injection member securement location defining a third position for passage of said projection upon movement thereof between said first and second positions.

11. A syringe assembly of claim 10 wherein said injection member securement location is positioned more proximal said one end of said barrel than said retention location whereby relative rotational movement between said cover and said injection holder causes relative movement of said cover with respect to said injection holder from said first position to said second position.

12. A syringe assembly of claim 11 wherein said channel is elongate having one end defining a first said exit/entry opening location, an opposed end defining a second said exit/entry location and said retention location being disposed between said first and second said entry/exit locations.

13. A syringe assembly of claim 12 where said channel further includes a first said injection member securement location disposed between said first exit/entry opening location and said retention location and a second said injection member securement location disposed between said second exit/entry opening location and said retention location.

14. A syringe assembly of claim 11 wherein said injection member is removably seated within said cover for movement therewith from said first position to said third position.

15. A syringe assembly of claim 6 wherein said injection holder is an elongate member including an open end for attachment to said barrel, an opposed neck for frictionally supporting said injection member and a central shaft therebetween.

16. A syringe assembly of claim 15 wherein said cover is removably secured to said central shaft of said injection holder.

17. A syringe assembly of claim 16 wherein said shaft of said injection holder includes said tortuous channel defining said keyway structure and wherein said cover includes said extending projection defining said key structure. having a pair of diametrically opposed said tortuous channels thereon, and wherein said cover includes a cylindrical portion having a pair of diametrically opposed said projections.

18. A syringe assembly of claim 17 wherein said shaft is generally cylindrical having a pair diametrically opposed said tortuous thereon, and wherein said cover includes a cylindrical portion having a pair of diametrically opposed said projections.

19. A syringe assembly of claim 15 wherein said injection member further includes:
    an elongate injection needle for percutaneous insertion; and
    an elongate needle support having a first end for supporting said needle and second hub end for frictional retention on said neck of said injection holder.

20. A syringe assembly of claim 15 wherein said injection member further includes:
    an elongate IV access device, said device including a first end for fluid delivery and a second hub end for frictional retention on said neck of said injection holder.

21. A syringe assembly of claim 1, wherein the cover includes an insert.

22. A syringe assembly of claim 1, wherein the injection holder includes a luer collar and the injection member includes a pair of wings for mating with one another to form a luer-lock syringe.

23. A fluid dispensing medical syringe comprising:

an elongate fluid containing barrel defining a longitudinal axis and opposed open ends;

a plunger movably supported in one end of said barrel for effecting said fluid dispensing;

an injection holder attached to the other of said open ends;

an injection member fictionally seatable on said injection holder;

a cover releasably supporting said injection member therein, said cover being movable with respect to said injection holder in relative rotative and axial directions so as to attach and remove said cover to said injection holder; and guide means for guiding said movement of said cover with respect to said injection holder such that selective said rotative movement of said cover causes said axial movement of said cover towards said injection holder prior to removal of said cover from said injection holder so as to assure said frictional seating of said injection member on said injection holder.

24. A syringe of claim 23 wherein said guide means includes a channel formed on one of said injection holder and said cover and a projection formed on the other of said injection holder and said cover, said projection being movable within said channel to effect said guided movement of said cover with respect to said injection holder.

25. A syringe of claim 24 wherein said channel defines:

a first projection accommodating position wherein said cover is attached to said injection holder;

a second projection accommodating position wherein said cover is removed from said injection holder; and a third projection accommodating position wherein said injection member supported by said cover is frictionally seated on said injection holder;

wherein movement of said cover from said first projection accommodating position to said second projection accommodating position causes movement of said cover to said third projection accommodating thereby frictionally seating said injection member on said injection holder.

26. A syringe of claim 25 wherein said channel defines a plurality of cam surfaces, each cam surface defines one of said first, second and third projection accommodating surfaces.

27. A syringe of claim 26 wherein said cam surfaces translate said rotational movement of said cover with respect to said injection holder to axial movement.

28. A syringe assembly for dispensing a fluid comprising:

a hollow barrel having opposed open ends defining a fluid-containing chamber therebetween;

a manually operable plunger insertable in one end of said barrel for movement within said chamber;

an injection holder attached to said other end of said barrel;

an injection member through which said fluid is dispensed in response to said movement of said plunger, said injection member being removably secured over a portion of said injection holder; and a cover for accommodating said injection member and being removably attachable to said injection holder, said cover being movable with respect to said injection holder from a first position where said cover is retained on said injection holder to a second position where said cover is removed from said injection holder and wherein movement of said cover from said first position to said second position assures said removable securement of said injection member to said injection holder, wherein said cover and said injection member include interfitting key and keyway structure for guiding movement of said cover between said first and second positions.

\* \* \* \* \*